US012653961B2

(12) United States Patent
Todesco et al.

(10) Patent No.: US 12,653,961 B2
(45) Date of Patent: Jun. 16, 2026

(54) DEVICE FOR INSERTING A NEEDLE FOR DISPENSING A PRODUCT IN A SITE

(71) Applicant: Nemera La Verpillière, La Verpilliere (FR)

(72) Inventors: Marc Todesco, Tignieu-Jameyzieu (FR); Julien Roux, Caluire et Cuire (FR); Nicolas Didier, Trept (FR); Guillaume Albrand, Brignais (FR); Sébastien Delvalac, Lyons (FR)

(73) Assignee: Nemera La Verpilliere, La Verpilliere (FR)

( * ) Notice: Subject to any disclaimer, the term of this patent is extended or adjusted under 35 U.S.C. 154(b) by 680 days.

(21) Appl. No.: 18/018,811

(22) PCT Filed: Jul. 27, 2021

(86) PCT No.: PCT/EP2021/071087
§ 371 (c)(1),
(2) Date: Mar. 13, 2023

(87) PCT Pub. No.: WO2022/023391
PCT Pub. Date: Feb. 3, 2022

(65) Prior Publication Data
US 2023/0302230 A1      Sep. 28, 2023

(30) Foreign Application Priority Data
Jul. 28, 2020    (FR) ...................................... 2007979

(51) Int. Cl.
*A61M 5/32*          (2006.01)
*A61M 5/158*         (2006.01)
(52) U.S. Cl.
CPC ... *A61M 5/3232* (2013.01); *A61M 2005/1585* (2013.01)

(58) Field of Classification Search
CPC ........... A61M 2005/1585; A61M 2005/14252; A61M 2005/14268
See application file for complete search history.

(56) References Cited

U.S. PATENT DOCUMENTS

2007/0093754 A1      4/2007   Mogensen et al.
2008/0319414 A1      12/2008  Yodfat et al.
(Continued)

FOREIGN PATENT DOCUMENTS

WO        2009039013 A1      3/2009
WO        2014011879 A2      1/2014

OTHER PUBLICATIONS

Written Opinion and International Search Report for Application No. PCT/EP2021/071087 dated Nov. 22, 2021 (English translation of International Search Report included).

*Primary Examiner* — Laura A Bouchelle
(74) *Attorney, Agent, or Firm* — Farber LLC

(57) ABSTRACT

The insertion device has a support wall on the site, a receiving body having a guiding housing, the needle housing, on which an insertion needle is mounted, movably mounted in the guiding housing between a pre-insertion position, at least one insertion position and at least one retracted position, a first return means stressed when the needle housing is in the pre-insertion position and driving the needle housing from the pre-insertion position to the at least one insertion position in released state, a second return means, stressed when the needle housing is in the pre-insertion position and in the at least one insertion position and driving the needle housing from the at least one insertion position to the at least one retracted position in released state.

20 Claims, 6 Drawing Sheets

(56)                    References Cited

U.S. PATENT DOCUMENTS

2009/0118592  A1*    5/2009   Klitgaard ............. A61B 5/6849
                                                        600/300
2016/0243302  A1      8/2016   Gyrn
2019/0365986  A1*   12/2019   Coiner .............. A61M 5/14248

* cited by examiner

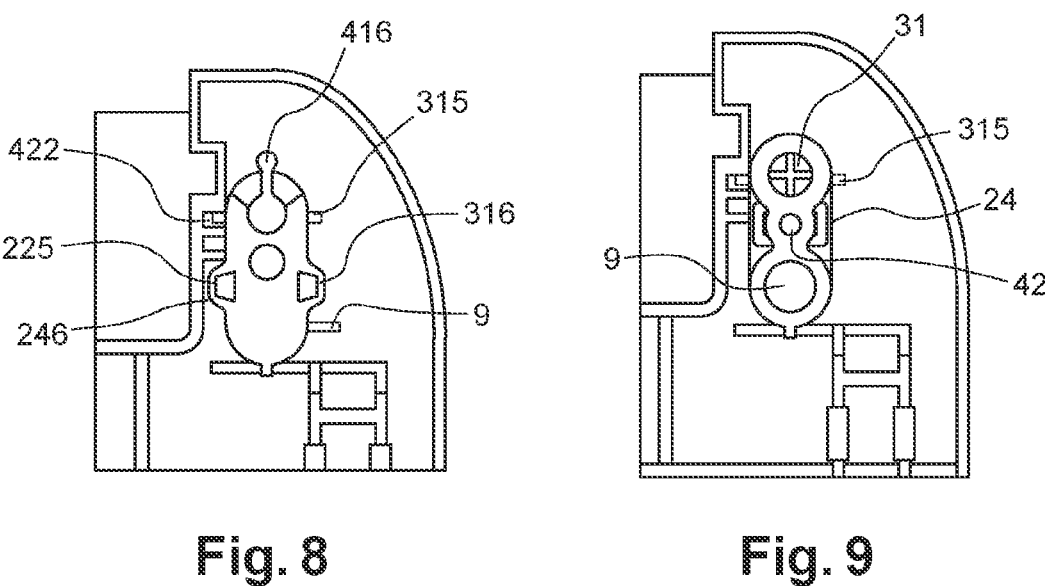
Fig. 8　　　　　Fig. 9
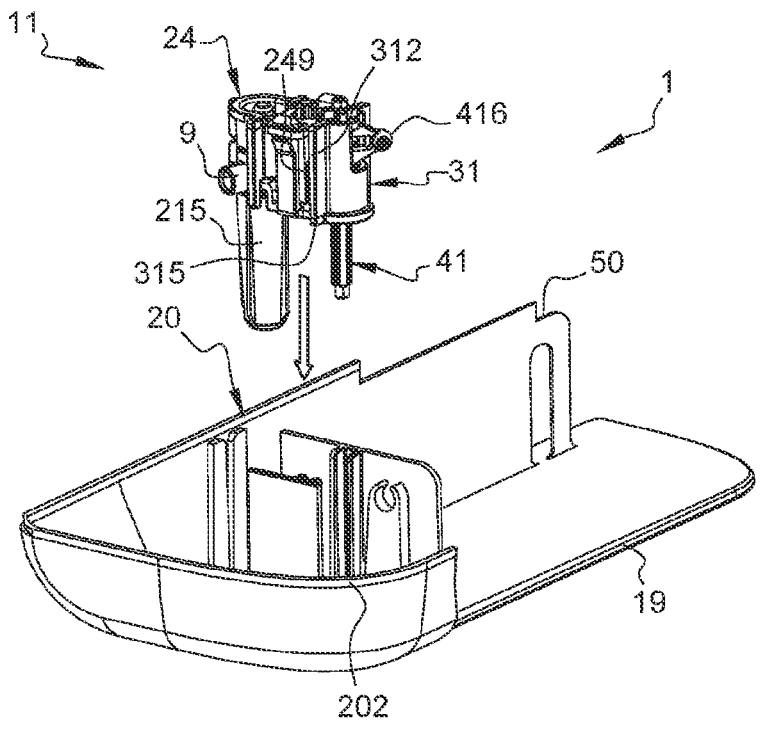
Fig. 10

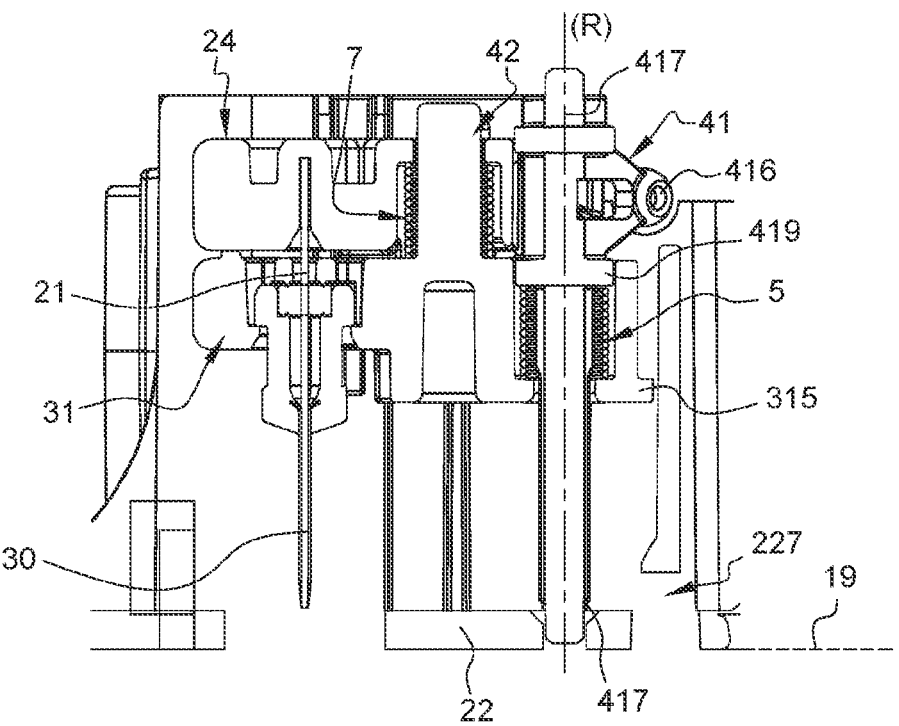
Fig. 11
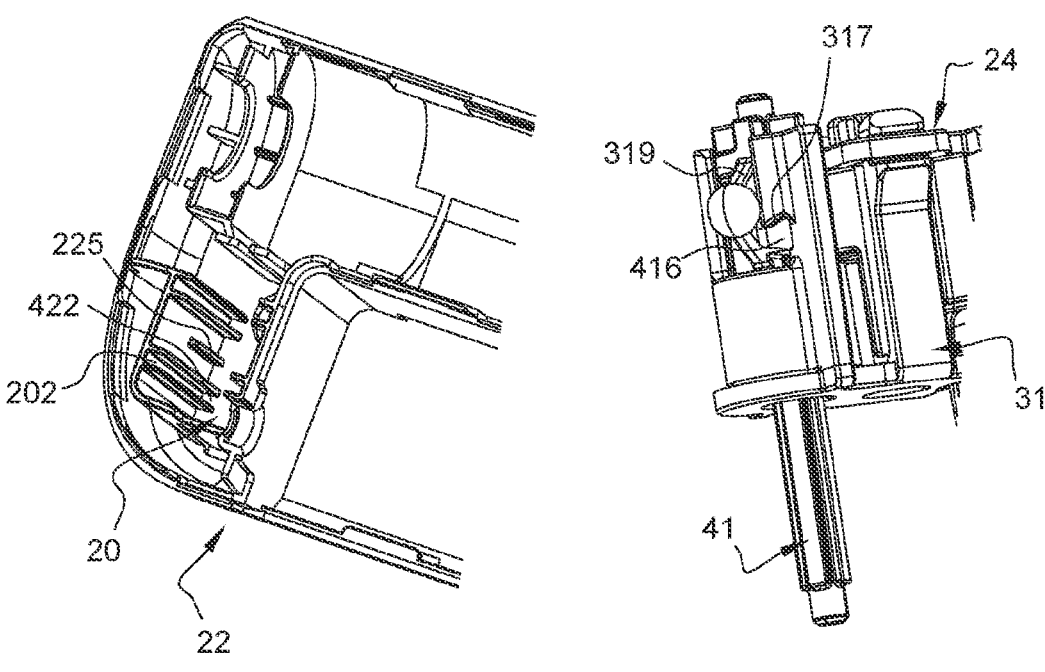
Fig. 12                    Fig. 13

DEVICE FOR INSERTING A NEEDLE FOR DISPENSING A PRODUCT IN A SITE

FIELD OF THE INVENTION

The invention relates to a device for inserting a needle into a site. The invention relates more particularly to a needle insertion device used to dispense a product into the site where the needle was inserted, especially by using a catheter or a cannula.

BACKGROUND OF THE INVENTION

The state of the art, in particular document WO2015164645 already describes a needle insertion device for inserting a catheter (or cannula) to dispense a medication. The insertion device described therein is used to convert a movement of a connection element driven by a torsion spring into a vertical translation of a needle housing in order to insert the needle and the catheter into the skin of a patient. More precisely, the torsion spring is mounted in a prestressed state. Once released, the torsion spring drives the connection element in a back and forth displacement, which moves the needle from its pre-insertion position to the insertion position, and then brings the needle back to the retracted position. Thus, the connection element comprises a first axis of rotation connected in translation to the needle housing and around which the torsion spring is mounted, and a second axis allowing a drive pin to slide in a camway attached to a body for receiving the insertion device. The connection element must firstly be assembled with the needle support, then the assembly is attached to the receiving body while ensuring to compress the torsion spring against a stop provided on the receiving body and to insert the drive pin in the camway. This implies various constraints regarding the assembly and operation of the insertion device.

The invention aims in particular to provide a needle insertion device that is simpler and more compact.

SUMMARY OF THE INVENTION

The invention therefore relates to a device for inserting a needle into a site, comprising:
- a support wall on the site,
- a receiving body having a guiding housing receiving a needle housing,
- the needle housing, on which an insertion needle is mounted, movably mounted in the guiding housing between
- a pre-insertion position in which the needle is retracted with respect to the support wall,
- at least one insertion position in which the needle protrudes with respect to the support wall, and
- at least one retracted position in which the needle is once again retracted with respect to the support wall,
- a first return means, configured to be stressed when the needle housing is in the pre-insertion position and to drive the needle housing from the pre-insertion position to the at least one insertion position in released state,
- a second return means, configured to be stressed when the needle housing is in the pre-insertion position and in the at least one insertion position and to drive the needle housing from the at least one insertion position to the at least one retracted position in released state.

Thus, it is proposed to use two separate return means in the insertion device, one allowing the needle housing to move from the pre-insertion position to the at least one insertion position, and the other to move the needle housing from the at least one insertion position to the at least one retracted position. The insertion device is therefore particularly simple and compact, avoiding, for example, a need to use a single torsion spring together with a relatively complex arrangement of axes of rotation and a camway. Thus, due to the second return means, the movement of the needle housing from the at least one insertion position to the at least one retracted position is optimised and faster.

Preferably, the first and second return means are stressed before using the insertion device. They are said to be prestressed. It is particularly interesting to use a prestressed return means, since there is no need to provide a complex and bulky mechanism in the insertion device to compress the return means, it suffices only to release it to exert an associated return force.

In addition, the use of a second prestressed return means allows the needle housing to retract automatically, which is especially advantageous, contrary to what is proposed, for example, in the device described in document WO2015/164648, in which retraction is activated manually.

According to other optional characteristics of the needle insertion device, taken alone or in combination:
- The needle insertion device comprises a catheter movably mounted with respect to the needle and a catheter holder adapted to move the catheter with the needle when the needle housing moves from its pre-insertion position to the at least one insertion position and to separate it from the needle so that its movement remains locked when the needle housing moves from the at least one insertion position to the at least one retracted position.

It is understood that the second return means is advantageously assembled between the catheter holder and the needle housing so as to drive the needle housing to the at least one retracted position, while keeping the catheter holder and therefore the catheter in a position in which the catheter protrudes with respect to the support wall.

It is also understood that the first return means is advantageously assembled between the catheter holder and the receiving body so as to drive the needle housing to the insertion position.
- The needle insertion device further comprises a first rod movably mounted in rotation about an axis of rotation R in a first rod housing of the receiving body, the axis of rotation R being parallel to a guiding axis G of the guiding housing receiving the needle housing, the catheter holder and the first rod comprising first releasable blocking means which, when released, allow the needle housing to move from the pre-insertion position to the at least one insertion position.

Thanks to the first blocking means, the catheter holder and the first rod can be positioned with respect to each other in two configurations:
- an engaged configuration, for example when the needle housing is in the pre-insertion position, in which the first blocking means cooperate and the first rod blocks in translation the catheter holder,
- a release configuration in which the first blocking means do not cooperate.

From the engaged configuration, the release configuration is obtained by rotating the first rod with respect to the catheter holder until the first blocking means do not cooperate longer.

Thus, the size of the insertion device is optimized since the first blocking means do not increase the size, for example in terms of height of the insertion device, regardless of their configuration.

A first part of the first blocking means is carried by the catheter holder and a second part of the first blocking means is carried by the first rod.

Advantageously, the first blocking means comprise at least one rib intended to cooperate with the at least one ledge and to slide in at least one groove.

Preferably, the rib is formed on the catheter holder and is configured, firstly, to cooperate with a peripheral ledge formed on the first rod and opening out onto a longitudinal peripheral groove of the first rod, then secondly, to slide in this longitudinal peripheral groove. Thus, in the engaged configuration, the rib is one of the first blocking means carried by the catheter holder, and which cooperates with another of the first blocking means carried by the first rod, corresponding to the peripheral ledge of the first rod opening out onto the longitudinal peripheral groove.

The first return means is mounted around or inside the first rod.

The first rod can therefore be used both for guiding when inserting the needle and for guiding the first return means. This part perform therefore two guiding functions, in addition to a function of releasing the first return means, thereby reducing the number of parts and therefore simplifying the insertion device and reducing its size.

Preferably, the first return means is a helical spring mounted around the first rod.

The first rod further comprises a protrusion intended to interact with an activating element to allow the first rod to rotate.

It is therefore understood that the activating element interacts with the protrusion of the first rod to allow a rotational movement of the first rod. This rotation of the first rod therefore allows the first rod to be in its release configuration in which the first blocking means do not cooperate longer and thus allows the release of the first return means making it possible for the needle housing to move from the pre-insertion position to the at least one insertion position.

Thus, the first rod can be rotated by the interaction of a protrusion with an activating element, the latter being mechanical or motorized.

The activating element may correspond to a muscle wire, a lever arm, an electric motor or a mechanical button intended to interact directly with the user, etc.

Preferably, the activating element is mechanical. In this case, insertion of the needle does not require the action of a motor and is based on a direct action by the user via, for example, an activation surface forming the activating element of the insertion device. Note that the activation surface can be accessed by the user when the needle insertion device is assembled and the needle housing is in the pre-insertion position. Similarly, in another embodiment, a simple muscle wire can be used as activating element. The use of this insertion device is therefore simple and requires little energy.

As an alternative, the activating element is an electric motor.

Thus, motorized insertion of the needle into the site can be triggered. It is understood that, in this case, the electric motor is not used to move the needle housing, this being carried out by the first return means, but as a trigger to insert the needle. In addition, advantageously, this electric motor can be used for other functions, such as controlling a product injection.

Optionally, the protrusion has the general shape of an arm which extends towards the outside of the first rod in a radial plane substantially perpendicular to the axis (R).

The needle insertion device comprises means for adjusting the position of the catheter holder with respect to the support wall when the needle housing is in the at least one insertion position.

The catheter holder can therefore be locked in position with respect to the support wall at different positions corresponding to different insertion positions of the needle housing. It is particularly interesting to be able to vary the needle housing insertion positions in order to vary, for example, the product injection depth, and thus to adapt the injection of product to the factors such as the patient's morphology or the type of injection required, for example.

The adjustment means may advantageously be means for adjusting the height of a ledge, carried by the receiving body, forming a stop with the catheter holder. The adjustment means may for example comprise a wheel or a screw-nut assembly that can be accessed by a user from the outside of the receiving body or the insertion device, or electronic control means.

The needle insertion device comprises a retractable locking means for locking the needle housing with respect to the catheter holder, the locking means preferably comprising:

a stop abutment carried by the catheter holder, and an elastic tab carried by the needle housing, the elastic tab of the needle housing being configured to be clipped under the stop abutment of the catheter holder when the needle housing is in the pre-insertion position, and to be deformed, when the needle housing is in the at least one insertion position, by a ledge carried by the receiving body, such that the needle housing is retracted from the catheter holder.

The locking means therefore allows the needle housing to be driven from the pre-insertion position to the at least one insertion position with the catheter holder, position in which the elastic tab of the needle housing is deformed by the ledge of the receiving body so as to release the needle housing from the catheter holder and so that the needle housing can leave the at least one insertion position and move to the at least one retracted position under the action of the second return means.

The needle insertion device further comprises a second rod mounted about a longitudinal axis L in a second rod housing of the receiving body, the longitudinal axis L being parallel to the guiding axis G of the guiding housing receiving the needle housing, the second return means being mounted around or inside the second rod.

The second rod can be used both for guiding when retracting the needle and for guiding the second return means. This part performs therefore two guiding functions, thereby reducing the number of parts and hence simplifying the insertion device and reducing its size. In addition, this configuration results in an particularly compact insertion device, in which the first return means and the second return means are arranged on each side of the needle, that only requires to have the height necessary to move the needle to insert it into a site.

Optionally, the second return means is a helical spring mounted around or inside the second rod.

In addition, the second rod can be movable in rotation about the longitudinal axis L, and the catheter holder and the second rod may comprise second releasable blocking means, adapted to cooperate together and which, when released, allow the needle housing to move from the at least one insertion position to the at least one retracted position.

Thus, the second rod comprises a function for releasing the second return means.

The second rod can also be used to perform an additional check when moving from the pre-insertion position to the insertion position since the second blocking means cooperate in the engaged configuration, while providing the above-mentioned advantages for the first rod.

Preferably, a first part of the second blocking means is carried by the catheter holder and a second part of the second blocking means is carried by the second rod.

The size of the insertion device is optimized since the second blocking means do not increase the size, for example in terms of height of the insertion device, regardless of their configuration.

Advantageously, the second blocking means comprise at least one rib intended to cooperate with at least one ledge and to slide in at least one groove.

Preferably, the rib is formed on the catheter holder and is configured, firstly, to slide on a peripheral ledge formed on the second rod and opening out onto a longitudinal peripheral groove of the second rod, then secondly, to slide in this longitudinal peripheral groove.

The second rod may further comprise a protrusion intended to interact with an activating element to allow the second rod to rotate, in a way similar to that described above for the first rod.

All the characteristics described for the protrusion and the activating element concerning the first rod apply to the protrusion and the activating element of the second rod.

The first return means and the second return means extend respectively along a first axis and a second axis that are parallel to a guiding axis of the guiding housing, the first axis and the second axis being offset transversally with respect to each other.

The needle extends along a needle axis that is parallel to the guiding axis, the needle axis being offset transversally with respect to the first and second axes.

The invention also relates to a method for assembling a needle insertion device, comprising a step of assembling the first return means, the second return means, the needle housing equipped with the needle, the second return means and the first return means being compressed between parts of the insertion device that are adapted to be moved with respect to each other when using the insertion device.

Advantageously, the assembly method comprises the following steps:

- assembling the second return means, the needle housing and a catheter holder equipped with a catheter, the second return means being compressed between the needle housing and the catheter holder,
- attaching the second return means, the needle housing and the catheter holder, with the first return means, on a receiving body, the first return means being compressed between the catheter holder and the receiving body.

The invention also relates to a system for dispensing a product into a site, comprising:

- a needle insertion device as described previously,
- a reservoir containing the product and, advantageously
- a pump connecting the reservoir to the insertion device to dispense the product to the site via the needle.

According to one embodiment, the product dispensing system may be portable. This allows the patient to move and perform simple activities while receiving the product which may, for example, be a medical treatment.

The invention also relates to a kit for assembling a system for dispensing a product into a site, comprising a needle insertion device as described previously.

According to a preferred embodiment, the assembly kit may comprise a disposable part comprising the needle insertion device as described previously and a reusable part comprising at least setting means and, optionally, means for controlling the needle insertion device.

In a preferred configuration, the disposable, or single-use, part is removably mounted on the reusable part. According to one embodiment, the assembly kit may comprise a pump to dispense the product to the site via the needle, the pump can be directly integrated into the disposable part or the reusable part.

Similarly, in another configuration, the assembly kit may comprise a reservoir containing the product to be injected, the reservoir being intended to be assembled with the disposable part and to be connected by the pump to the insertion device to dispense product into a site.

Lastly, in one embodiment of the invention, a motor can be integrated in the disposable part. Preferably, the motor is an electric motor.

The assembly kit allows, for example, the medical staff or the patient to have everything needed to perform the treatment or to provide the medical staff or the patient with some of the items required by the system for dispensing a product into a site, in particular one or more disposable parts.

BRIEF DESCRIPTION OF THE DRAWINGS

The invention will be better understood on reading the following description, given solely by way of example and with reference to the accompanying drawings in which:

FIG. 8 is a view from above of the insertion device according to the second embodiment of the invention;

FIG. 9 is a cross-sectional view along A-A of the insertion device shown on FIG. 5, mounted on the receiving body of the insertion device according to the second embodiment;

FIG. 10 is a view of the insertion assembly shown on FIG. 5, represented during its installation on the receiving body of the insertion device according to the second embodiment of the invention;

FIG. 11 is a longitudinal cross-sectional front view of the insertion device according to the second embodiment;

FIG. 12 is a perspective view from above of a part of the receiving body shown on FIG. 9;

FIG. 13 is a side view of the insertion assembly shown on FIG. 5.

DETAILED DESCRIPTION OF THE INVENTION

Figures 1, 2:
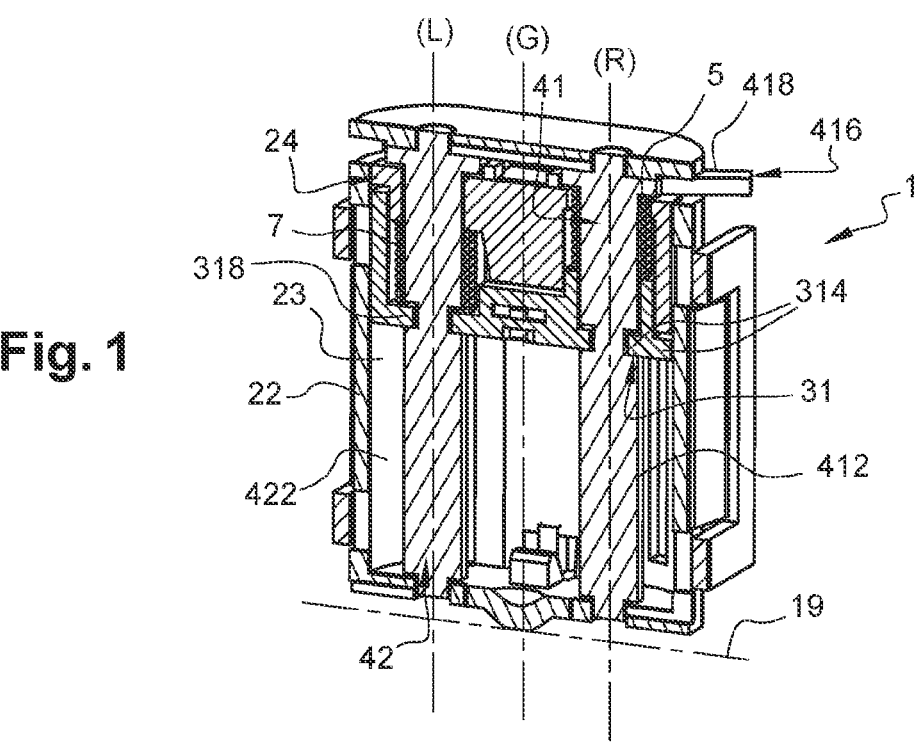
FIG. 1 is a longitudinal cross-sectional front view of a needle insertion device according to a first embodiment of the invention, the needle housing being in the pre-insertion position.
FIG. 2 is a rear view of a part of the insertion device shown on FIG. 1 comprising the second return means.
Figure 3A:
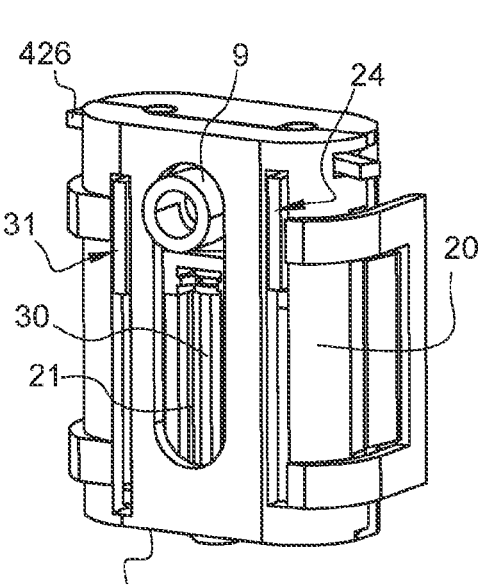
FIG. 3a is is a rear view of the insertion device shown on FIG. 1 represented with the needle housing in the pre-insertion position.
Figure 3B:
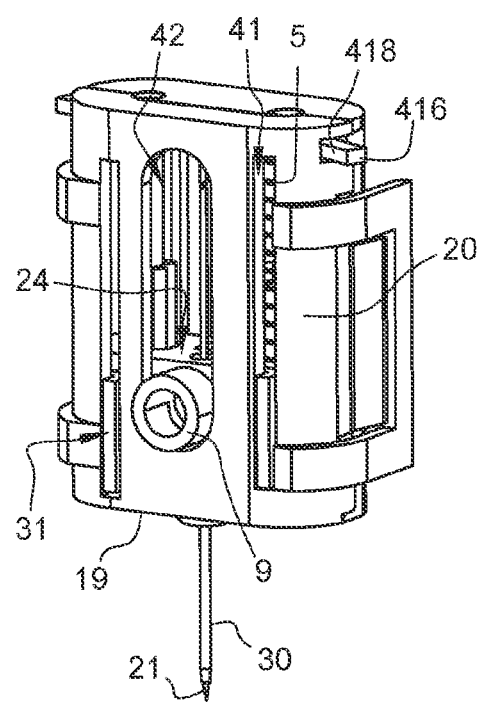
FIG. 3b is a rear view of the insertion device shown on FIG. 1 represented with the needle housing in an insertion position.
Figure 3C:
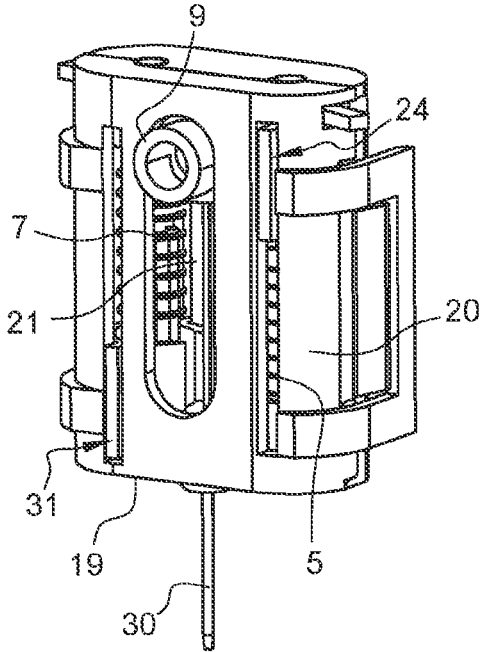
FIG. 3c is a rear view of the insertion device shown on FIG. 1 represented with the needle housing in a retracted position.
Figure 4:
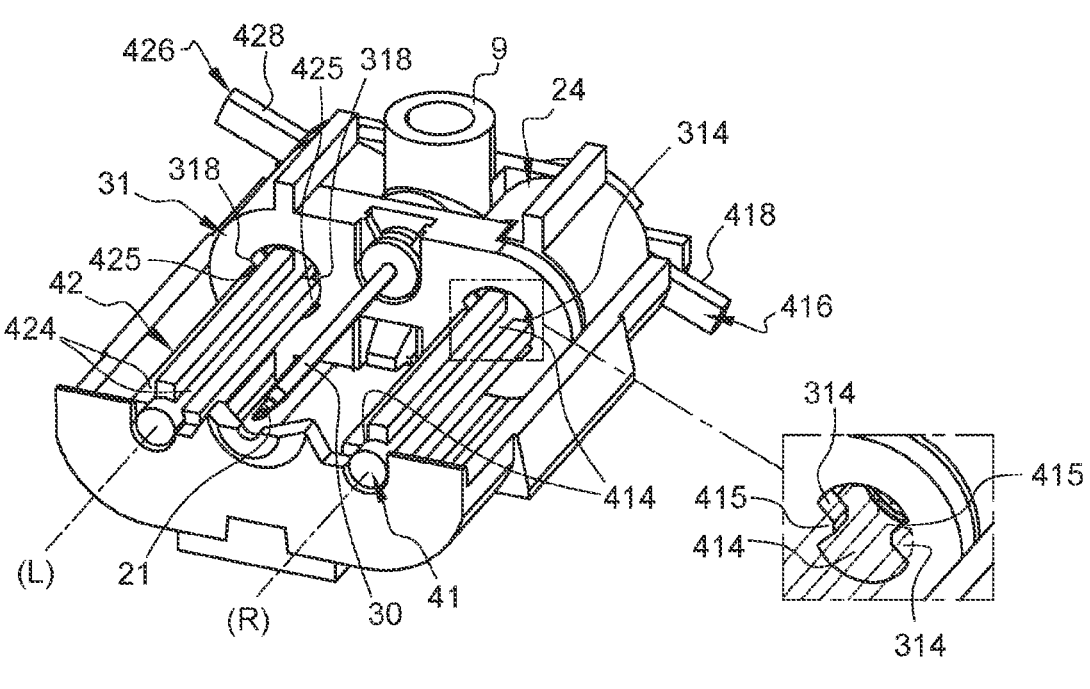
FIG. 4 is a view from below of the rear side of the insertion device shown on FIG. 1 represented in the pre-insertion position.
Figure 7:
FIG. 7 is a view from below of the insertion assembly shown on FIG. 5 represented in the pre-insertion position.
Figure 5:
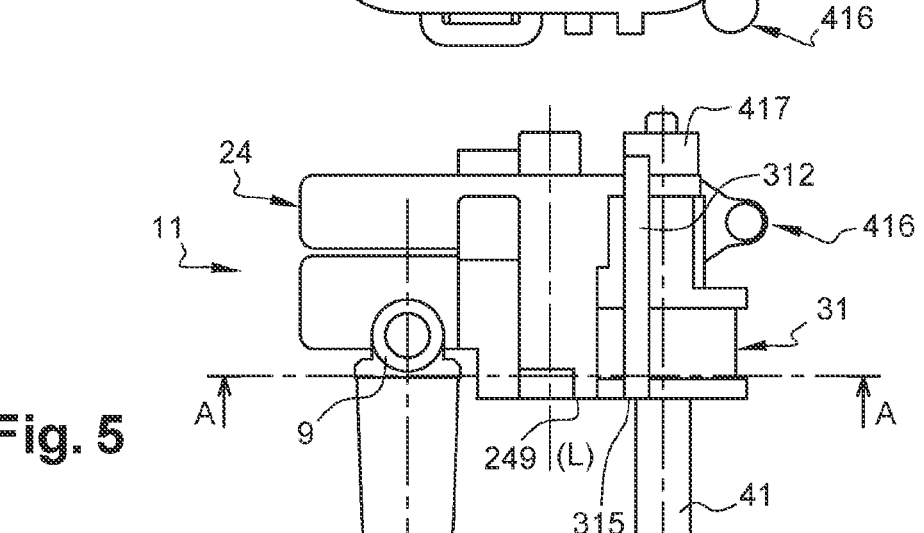
FIG. 5 is a front view of an insertion assembly of a needle insertion device according to a second embodiment of the invention, the needle housing being in the pre-insertion position.

FIGS. 1 to 4 show an insertion device according to one embodiment of the invention, designated by the general reference 1. The insertion device 1 comprises a body having a support wall 19 intended to be placed in direct contact with the skin of a patient. FIGS. 1, 2 and 4 are partial views of the insertion device 1 because the insertion device 1 may comprise a lid or housing forming the body of the insertion device 1 and forming a closed space with the support wall 19 so that the elements which will be described below cannot be seen or accessed from the outside of the insertion device 1. The housing 20 is shown on FIGS. 3a, 3b and 3c.

The insertion device 1 is configured to inject a product, preferably liquid, in particular a medication, into a site in a relatively long time, generally several minutes, or even several hours. For example, the insertion device 1 can therefore be carried by a patient during the injection, for example on the waist.

The products, in particular pharmaceutical products, likely to be used by the dispensing device include, for example, formulations containing at least one active ingredient such as peptides, proteins, hormones, active ingredients of biological origin, nucleotide-based active ingredients, such as for example DNAs, RNAs or oligonucleotides, active ingredients of molecular weight up to 1500 Da, polysaccharides, vaccines, enzymes, antibodies, nutritional formulae and other substances or a mixture thereof.

The products, in particular pharmaceutical products, likely to be used by the dispensing device can be used for the treatment and/or prevention of diabetes, thromboses, cardiovascular diseases, such as coronary syndrome, angina, myocardial infarction, cancers, macular degeneration, inflammations, atherosclerosis and/or rheumatoid arthritis.

These active ingredients may include, but are not limited to, insulins, insulin analogues such as insulin lispro or insulin glargine, insulin derivatives, C-peptide, GLP-1 receptor agonists such as dulaglutide or liraglutide, glucagon, glucagon analogues, glucagon derivatives, gastric inhibitor polypeptides (GIP), GIP analogues, GIP derivatives, oxyntomodulin analogues, oxyntomodulin derivatives, therapeutic antibodies, such as monoclonal antibodies and any therapeutic agent that can be delivered by the above device, as well as a pharmaceutically acceptable salt and/or solvate and/or hydrate of the active ingredients listed above. The medication as it is used in the device can be formulated with one or more excipients.

In particular, the products may comprise a peptide for the treatment and/or prevention of diabetes.

In particular, the product may comprise at least one human insulin or an insulin derivative or analogue such as for example glucagon-like peptide (GLP-1) or a GLP-1 analogue or derivative, or exedin-3, exedin-4 or one of their analogues or derivatives, or Gly(A21), Arg(B31), Arg(B32) human insulins; Lys(B3), Glu(B29) human insulins; Lys(B28), Pro(B29) human insulins, Asp(B28) human insulins, B29-N-myristoyl-des(B30) human insulins; B29-N-palmitoyl-des(B30) human insulins; B29-N-myristoyl human insulins; B29-N-palmitoyl human insulins; B28-N-myristoyl LysB28ProB29 human insulins; B28-N-palmitoyl-LysB28ProB29 human insulins; B30-N-myristoyl- ThrB29LysB30 human insulins; B30-N-palmitoyl-ThrB29LysB30 human insulins; B29-N—(N-palmitoyl-Y-glutamyl)-des(B30) human insulins; B29-N—(N-lithocholyl-Y-glutamyl)-des(B30) human insulins; B29-N-(ω-carboxyheptadecanoyl)-des(B30) human insulins and B29-N-(ω-carboxyheptadecanoyl) human insulins and/or a pharmaceutically acceptable salt and/or solvate and/or hydrate of the insulins listed above.

In particular the product may comprise at least one hormone such as for example the hypophyseal or hypothalamic hormones such as for example the gonadotropins (follitropins, lutropins, choriongonadotropins, menotropins), somatropins or somatotropins, desmopressins, terlipressins, gonadorelins, triptorelins, leuprorelins, buserelins, nafarelins, goserelins and/or a pharmaceutically acceptable salt and/or solvate and/or hydrate of the hormones listed above.

In particular the product may comprise at least one polysaccharide such as for example a glucosaminoglycan, a hyaluronic acid, a heparin, a low-molecular-weight heparin or a heparin derivative, a sulphated or polysulphated polysaccharide, and/or a pharmaceutically acceptable salt and/or solvate and/or hydrate of the polysaccharides listed above.

The pharmaceutically acceptable salts are for example the acid addition salts, such as for example the HCl or HBr salts, and the basic salts, such as for example the salts composed of an alkali cation such as Na+, K+, or Ca2+, or an ammonium ion of type N+(R1)(R2)(R3)(R4), where R1, R2, R3 and R4 represent independently of each other: a hydrogen atom, an optionally substituted alkyl group (C1-C6), an optionally substituted alkenyl group (C2-C6), an optionally substituted aryl group (C6-C10), or an optionally substituted heteroaryl group (C6-C10). Other examples of pharmaceutically acceptable salts are well known by those skilled in the art.

The insertion device 1 of FIGS. 1 to 4 comprises a receiving body 22 having a guiding housing 23 defining a guiding axis (G). The guiding axis (G) can be designed to be substantially perpendicular to the support wall 19 or according to any other inclination suitable for inserting a needle 21 carried by a needle housing 24 and/or for injecting the product. The needle housing 24 is provided with a distribution channel 9, as shown for example on FIG. 4, to transfer product through the needle housing 24.

The receiving body 22 also comprises a ledge 225 in its lower part.

The needle housing 24 is movably mounted in the guiding housing 23 between a pre-insertion position, shown on FIG. 3a, in which the needle 21 is retracted with respect to the support wall 19, at least one insertion position, shown on FIG. 3b, in which the needle 21 protrudes with respect to the support wall 19, and at least one retracted position, shown on FIG. 3c, in which the needle 21 is once again retracted with respect to the support wall 19.

The insertion device 1 also comprises:

a first return means 5, represented in this case by a first helical spring, configured to be stressed when the needle housing 24 is in the pre-insertion position and to drive the needle housing 24 from the pre-insertion position to the at least one insertion position in released state, a second return means 7, represented in this case by a second helical spring, configured to be stressed when the needle housing 24 is in the pre-insertion position and in the insertion position and to drive the needle housing 24 from the insertion position to the retracted position in released state.

The first and second springs 5 and 7 are in this case prestressed before using the insertion device 1.

The insertion device 1 also comprises a catheter 30 carried by a catheter holder 31. The catheter 30 is movably mounted with respect to the needle 21. The catheter holder 31 is adapted to move the catheter 30 with the needle 21 when the needle housing 24 moves from its pre-insertion position to its insertion position and to separate it from the needle 21 so that the movement of the catheter 30 remains blocked when the needle housing 24 moves from its insertion position to its retracted position. The first spring 5 is assembled between the receiving body 22 and the catheter holder 31, so as to drive the needle housing 24 to the insertion position. The spring 7 is assembled between the catheter holder 31 and the needle housing 24 so as to drive the needle housing 24 to the retracted position, while keeping the catheter 30 in a position in which it protrudes with respect to the support wall 19.

The receiving body 22 comprises a first housing 412 for a first rod 41 movably mounted in rotation about an axis of rotation (R). The axis of rotation (R) is parallel to the guiding axis (G) of the guiding housing 23.

The receiving body 22 also comprises a second housing 422 for a second rod 42 mounted about a longitudinal axis (L). The longitudinal axis (L) is parallel to the guiding axis (G).

The first rod 41 further comprises a protrusion 416 having an activation surface 418. When the user presses on the activation surface 418, the protrusion 416 interacts via its activation surface 418, so as to drive the protrusion 416 in rotation. The rotation can take place in both directions of rotation. This rotates the first rod 41. Thus, the protrusion 416 interacts via its activation surface 418 to rotate the first rod 41. In this case, the activating element is therefore mechanical.

The catheter holder 31 comprises a first pair of ribs 314. The first rod 41 comprises a pair of peripheral ledges 415 opening out onto a pair of longitudinal peripheral grooves 414. These elements are shown on FIG. 4. The first pair of ribs 314 and the pair of grooves 414 of the first rod 41 have complementary shapes. In the pre-insertion position, as shown on FIG. 4, the first pair of ribs 314 and the pair of grooves 414 of the first rod 41 do not cooperate. The first pair of ribs 314 therefore abuts against the pair of ledges 415 of the first rod 41. The first pair of ribs 314 of the catheter holder 31 thus locks in translation the needle housing 24 and the catheter holder 31. The first pair of ribs 314 and the pair of ledges 415 of the first rod 41 therefore form blocking means intended to cooperate. In an engaged configuration, shown on FIG. 4, the blocking means 314, 415 cooperate and the first rod 41 blocks in translation the catheter holder 31 and the needle housing 24. The rotation of the first rod 41 releases the first pair of ribs 314 from the pair of ledges 415 of the first rod 41. The first blocking means 314, 415 are therefore releasable. In release configuration, the first pair of ribs 314 interacts with the pair of grooves 414 of the first rod 41, and slides therein, allowing the catheter holder 31 to translate, under the effect of the force of the first spring 5. Releasing the blocking means 314 and 415 therefore allows the needle housing 24 to move from the pre-insertion position to the insertion position.

The insertion device 1 comprises a means for locking the needle housing 24 with respect to the catheter holder 31. This locking means, shown on FIG. 2, comprises a stop abutment 316 carried by the catheter holder 31 and an elastic tab 246 carried by the needle housing 24. The elastic tab 246 of the needle housing 24 is clipped under the stop abutment 316 of the catheter holder 31 when the needle housing 24 is in the pre-insertion position. Thus, when the blocking means 314, 415 are released and the catheter holder 31 is driven in translation, it drives the needle housing 24 at the same time. When the needle housing 24 is in the insertion position, the elastic tab 246 of the needle housing 24 is deformed by the ledge 225 of the receiving body 22, such that the needle housing 24 is retracted from the catheter holder 31. The locking means 246, 316 is therefore retractable. The locking means 246, 316 thus allows the needle housing 24 to be driven from the pre-insertion position to the insertion position with the catheter holder 31, position in which the elastic tab 246 of the needle housing 24 is deformed by the ledge 225 of the receiving body 22 so as to release the needle housing 24 from the catheter holder 31. This allows the needle housing 24 to leave the insertion position and move up to the retracted position under the action of the second spring 7.

The first spring 5 is mounted around the first rod 41. The first rod 41 can be used both for guiding when inserting and retracting the needle 21 and for guiding and releasing the first spring 5.

The spring 7 is mounted around the second rod 42. The second rod 42 can be used both for guiding when retracting the needle 21 and for guiding the second spring 7. In addition, the second rod 42 is movable in rotation about the longitudinal axis (L). Like the first rod 41, the second rod 42 comprises a protrusion 426 having an activation surface 428. When the user presses on the activation surface 428, the protrusion 426 of the second rod 42 interacts via its activation surface 428, so as to drive the protrusion 426 of the second rod 42 in rotation. This rotates the second rod 42. Thus, the protrusion 426 of the second rod 42 interacts via the activation surface 428 to rotate the second rod 42.

The insertion device 1 also comprises second releasable blocking means 318, 425 carried respectively by the catheter holder 31 and the second rod 42. Like the first releasable blocking means between the first rod 41 and the catheter holder 31, these second blocking means comprise a second pair of ribs 318 of the catheter holder 31 and a pair of peripheral ledges 425 of the second rod 42. The second rod 42 also comprises a pair of longitudinal peripheral grooves 424 opening out onto the pair of ledges 425 of the second rod 42. In an engaged configuration, shown on FIG. 4, the second blocking means 318, 425 cooperate and the second rod 42 blocks in translation the catheter holder 31. The rotation of the second rod 42 releases the second pair of ribs 318 from the pair of ledges 425 of the second rod 42. Releasing the second blocking means 318, 425, due to the rotation of the second rod 42, allows the needle housing 24 to move from the insertion position to the retracted position.

The second spring 7 is mounted around the second rod 42. The second rod 42 can be used for guiding when inserting and retracting the needle, and for guiding and releasing the second spring 7. The second rod 42 can also be used to release the first spring 5. Thus, if the second blocking means 318, 425 are not released, the movement of the catheter holder 31 remains blocked on the side of the second rod 42 since the second pair of ribs 318 carried by the catheter holder 31 and the pair of ledges 425 of the second rod 42 cooperate.

The insertion device 1 also comprises means, not shown, for adjusting the position of the catheter holder 31 with respect to the support wall 19 when the needle housing 24 is in the insertion position. The adjustment means can be means for adjusting the height of the ledge 225 of the receiving body 22. The means for adjusting the position of the catheter holder 31 may for example comprise a wheel or a screw-nut assembly that can be accessed by a user from the outside of the receiving body, or electronic control means.

FIGS. 3*a* to 3*c* show the various operating steps of the insertion device 1, which will be described as follows: when the insertion device 1 is ready to be used by a patient or by a member of the medical staff, the needle housing 24 is in a pre-insertion position (FIG. 3*a*) in which the needle 21 is retracted with respect to the support wall 19.

When the insertion device 1 is positioned on a site to be injected, the support wall 19 is, for example, in direct contact with the site. The patient or a member of the medical staff activates the rotation of the first and second rods 41, 42 by acting on the protrusions 416 and 426 of the first and second rods 41, 42. Consequently, the first and second pairs of ribs 314, 318 of the catheter holder 31 do not interact longer with the pairs of ledges 415, 425 of the first and second rods 41, 42. The catheter holder 31 and the needle housing 24 can then translate to the insertion position of the needle housing 24, under the effect of the first spring 5. In the insertion position, shown on FIG. 3*b*, the needle 21 and the catheter 30 are inserted into the insertion site.

As a variant, the device comprises a single protrusion which, when it is moved, activates the rotation of the first and second rods.

In the insertion position, the elastic tab 246 of the needle housing 24, which was clipped under the abutment stop 316 of the catheter holder 31, is deformed by the ledge 225 of the receiving body 22, such that the needle housing 24 is retracted from the catheter holder 31. The catheter holder 31 remains in position under the action of the first spring 5, while the needle housing 24 moves back up to the retracted position (FIG. 3*c*), under the effect of the spring 7. The injection can then start since the catheter 30 remains in position.

In one embodiment of the invention, the insertion device 1 may comprise control means, not shown, to indicate when the ledge 225 of the receiving body 22 has been reached.

Advantageously, the control means comprise at least one distance sensor and/or at least one displacement sensor. The at least one distance sensor and/or the at least one displacement sensor can be inductive, capacitive, based on optics, ultrasounds or microwaves, or be optoelectronic.

The remainder of the description presents an insertion device according to a second embodiment of the invention, as shown on FIGS. 5 to 12. On the various figures, the means performing the same function are designated by the same numerical reference, unless otherwise indicated in the description.

The differences between the first embodiment and the second embodiment will be described below.

In the second embodiment, shown on FIGS. 5 to 12, the insertion device 1 comprises an insertion assembly 11 adapted to be integrated in a housing 20 forming a receiving body 22 of the insertion assembly 11 and advantageously the support wall 19 of the insertion device 1.

The insertion device 11 comprises a needle housing 24 and a catheter holder 31.

Figure 6:
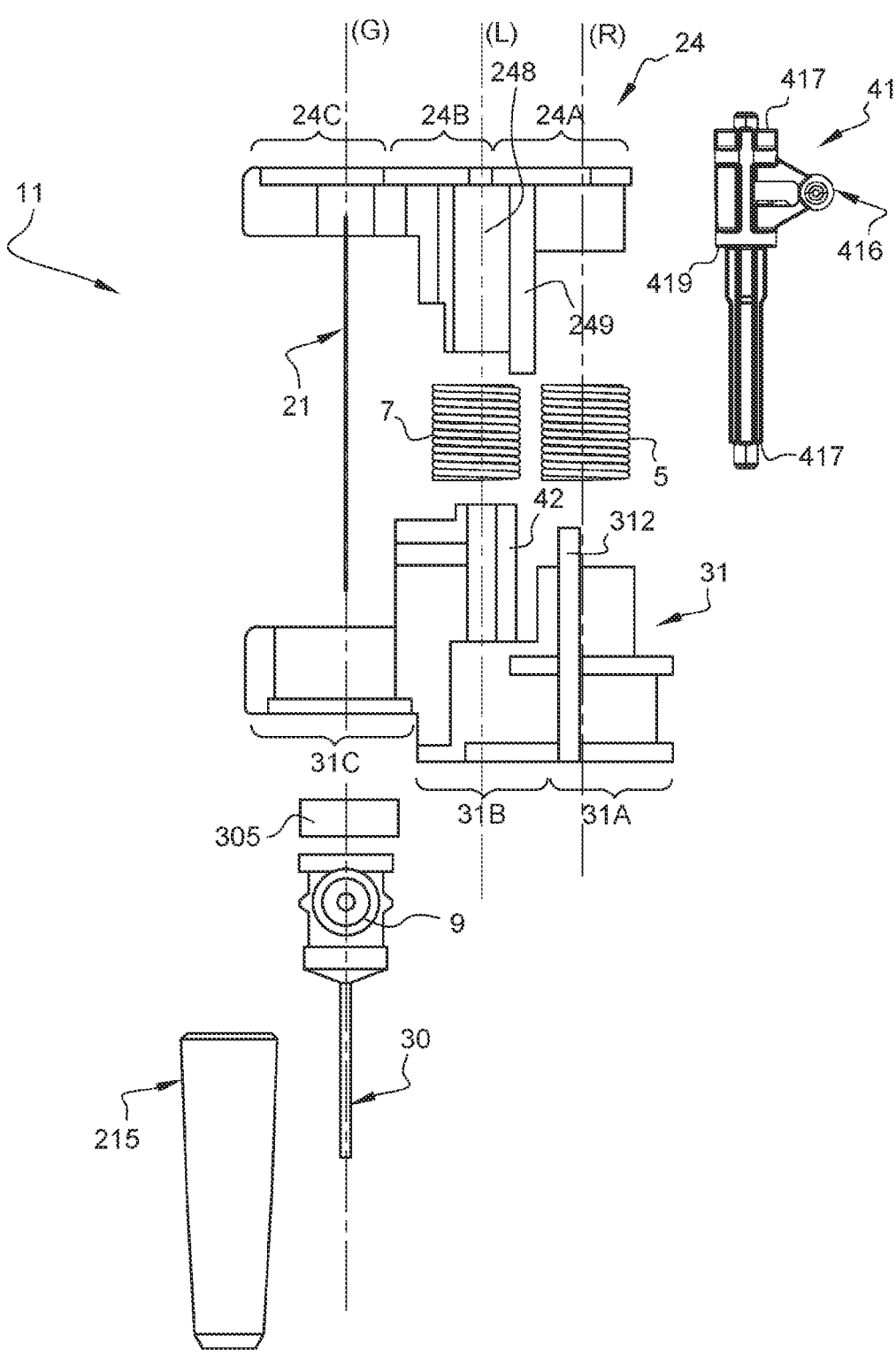
FIG. 6 is an exploded view of the insertion assembly shown on FIG. 5.

A protective cap 215 protecting the needle 21 is shown on FIGS. 5, 6, 7 and 10. FIG. 6 also shows the septum 305 of this catheter 30.

The needle housing 24 is adapted to be movably mounted in the receiving body 22 between the pre-insertion position, the insertion position and the retracted position.

The needle housing 24 and the catheter holder 31 are adapted to be assembled together and to move together to the pre-insertion position of the needle housing 24, in which the needle 21 is retracted with respect to the support wall 19, and when the needle housing 24 moves from the pre-insertion position until the needle housing 24 reaches the insertion position in which the needle housing 24 is separated from the catheter holder 31.

More precisely, the insertion assembly 11 comprises a means for locking the needle housing 24 with respect to the catheter holder 31. This locking means comprises a retaining means 246 carried by the needle housing 24 and an elastic tab 316 carried by the catheter holder 31. The tab 316 is configured to cooperate with the retaining means 246 when the needle housing 24 is in the pre-insertion position, and to be deformed, when the needle housing 24 is in the at least one insertion position, by a ledge 225 carried by the receiving body 22, shown on FIG. 12, such that the needle housing 24 is retracted from the catheter holder 31.

As a variant, the needle housing comprises the elastic tab and the catheter holder comprises the retaining means.

The insertion assembly also comprises first 5 and second 7 return means substantially similar to those of the first embodiment and also called first and second springs in the remainder of the document.

The insertion assembly comprises a first rod 41 received in a receiving through hole formed in the catheter holder 31. The first rod 41 is movable in rotation with respect to the catheter holder 31 about an axis (R) that is parallel to the guiding axis (G).

The insertion assembly 11 comprises a second rod 42 for guiding the needle housing 24 when it moves from the insertion position to the retracted position. The second rod 42 is for example formed by the needle housing 24 or the catheter holder 31.

When the blocking means are released and the catheter holder 31 is driven in translation, it drives the needle housing 24 at the same time. When the needle housing 24 is in the insertion position, the elastic tab 316 of the catheter holder 31 is deformed by the ledge 225 of the receiving body 22, such that the needle housing 24 is retracted from the catheter holder 31. The locking means 246, 316 is therefore retractable. The locking means 246, 316 thus allows the needle housing 24 to be driven from the pre-insertion position to the insertion position with the catheter holder 31, position in which the elastic tab 316 of the catheter holder 31 is deformed by the ledge 225 of the receiving body 22 so as to release the needle housing 24 from the catheter holder 31. This allows the needle housing 24 to leave the insertion position and move up to the retracted position under the action of the second spring 7.

The first spring 5 is mounted around the first rod 41. The first rod 41 can be used both for guiding when inserting and retracting the needle and for guiding and releasing the first spring 5. The first spring 5 is positioned between the catheter holder 31 and a stop 419 formed on the first rod 41, the first rod 41 preferably being fixed in translation with respect to the receiving body 22 unlike the catheter holder 31 and the needle housing 24. The first spring 5 is assembled so as to drive the needle housing 24 to the insertion position.

Advantageously, the first rod 41 comprises two ends along the axis of rotation (R), adapted to cooperate with the receiving body 22, such that the first rod 41 is fixed in translation along the axis of rotation (R) with respect to the receiving body 22. The first rod 41 comprises for example at each end a protrusion 417 adapted to be received in a complementary housing provided in the receiving body 22.

The first rod 41 is movable in rotation with respect to the receiving body 22 about the axis of rotation (R) that is parallel to the guiding axis (G).

In the second embodiment, in the pre-insertion position, the first rod 41 is associated with the catheter holder 31 by means of a bayonet type attachment system between the first rod 41 and the catheter holder 31. The rod 41 comprises for example a means for blocking the catheter holder 31 and in particular a contact stop for the catheter holder preventing the translation of the catheter holder 31 along the guiding axis (G). The blocking means is for example formed by the protrusion 416 and cooperates with the catheter holder 31 to block in translation the catheter holder 31 and the needle housing 24.

The rotation of the first rod 41 when the insertion device 1 is activated releases the catheter holder 31 which is no longer vertically resting against the contact stop 416 and moves under the effect of the force exerted by the first spring 5.

More precisely, the catheter holder 31 comprises for example a groove provided with a horizontal portion 317 for receiving the blocking means 416 in the pre-insertion position and a vertical portion 319 allowing the blocking means and therefore the protrusion 416 to move after activating the insertion device 1. After activating the insertion device 1, the blocking means and therefore the protrusion 416 moves from the horizontal portion 317 to the vertical portion 319, then crosses the vertical portion 319 as the catheter holder 31 and the needle housing 24 move to the insertion position under the force of the spring 5. The blocking means 416 is therefore releasable. The blocking means 416 therefore defines a configuration for blocking and a configuration for releasing the catheter holder 31 and therefore the needle housing 24. The blocking means 416 therefore allows the needle housing 24 to move from the pre-insertion position to the insertion position.

The second spring 7 is assembled between the catheter holder 31 and the needle housing 24 so as to drive the needle housing 24 to the retracted position, while keeping the catheter 30 in a position in which it protrudes with respect to the support wall 19.

The second spring 7 is mounted around the second rod 42. The second rod 42 can be used both for guiding when retracting the needle 21 and for guiding the second spring 7. Unlike the first embodiment, the second rod 42 is fixed in rotation about the longitudinal axis (L).

The second rod 42 is for example received in a through hole 248 formed by the needle housing 24 when the needle housing 24 is in the pre-insertion position and in the insertion position.

The second rod 42 is for example formed by a part of the catheter holder.

The receiving body 22 comprises members 202 for fastening the insertion assembly 11 which define a space 422 for receiving the second rod 42, also referred to as the second housing 422.

The catheter holder 31 is provided with a distribution channel 9, to transfer product into the catheter 30. The catheter holder 31 remains for example in position under the action of the first spring 5 once the needle housing 24 has moved from the insertion position to the retracted position. In the second embodiment, the distribution channel 9 is used to dispense the product to the patient without the product going through the needle 21, thereby making it simpler to dispense product to the patient while guaranteeing a high level of health safety.

Advantageously, the catheter holder 31 comprises a member for immobilizing the catheter holder with respect to the receiving body 22 when the needle housing 24 moves to the insertion position. The immobilization member comprises for example a protrusion 315 adapted to be received in a housing 227 of complementary shape, provided in the receiving body 22, when the needle housing 24 is in the insertion position. The immobilization member 315, when it cooperates with the receiving body 22, in other words when the needle housing 24 moves to the insertion position, immobilizes the catheter 30 in the receiving body 22 in a product dispensing position and guarantees that in the event of failure of the first spring 5, the catheter holder 31 will be kept in the product dispensing position. In this variant, the catheter holder 31 remains for example in position under the action of the immobilization member 315 once the needle housing 24 has moved from the insertion position to the retracted position. The immobilization member 315 guarantees the safety of the system since it prevents the catheter holder 31 from accidentally driving the catheter 30 outside the insertion site.

In the second embodiment, the second rod 42 is positioned between the first rod 41 and the needle 21, while in the first embodiment, the needle 21 is positioned between the first 41 and second 42 rods.

Advantageously, the housing 20 is adapted to receive the insertion assembly 11 and a reservoir containing the product to be injected.

Also advantageously, the housing 20 comprises tracks 202 corresponding to the members 202 for fastening the insertion assembly 11, adapted to receive the needle housing 24 and catheter holder 31 which comprise guiding portions 249, 312 adapted to move along said tracks 202.

Advantageously, regardless of the embodiment considered, the insertion device 1 is adapted to be integrated in a system for dispensing a product into a site, comprising the insertion device 1 and a reservoir containing the product.

In the two embodiments described, the first 5 and second 7 return means extend respectively along a first axis (R) and a second axis (L) that are parallel to the guiding axis (G). Advantageously, the first axis (R) and the second axis (L) are offset transversally with respect to each other. In other words, the first 5 and second 7 return means are not coaxial. The needle 21 and the catheter 30 are coaxial.

More generally, in the two embodiments described, the needle 21, the first return means 5 and the second return means 7 are offset transversally with respect to each other. The needle 21, the first return means 5 and the second return means 7 are therefore not coaxial and define needle axes (G), first axis (R) and second axis (L) offset transversally with respect to each other. Such an architecture simplifies the architecture of the insertion device 1 and avoids concentrating all the functions of this device along the same axis, which would considerably increase the vertical size and the complexity.

Also advantageously, the catheter holder 31 and the needle housing 24 each comprise first 24A, 31A, second 24B, 31B and third 24C, 31C respective portions, the first 24A, second 24B and third 24C portions of the needle housing 24 extending respectively coaxially with respect to the first 31A, second 31B and third 31C portions of the catheter holder 31 and extending respectively substantially coaxially with respect to the first axis (R), second axis (L) and needle axis (G). The first portions 24A, 31A are adapted to be associated with the first rod 41 and with the first return means 5, the second portions 24B, 31B are adapted to be associated with the second return means 7, and the third portions 24C, 31C are adapted to be associated with the needle 21. More precisely, the third portion 24C is adapted to carry the needle while the third portion 31C defines a housing through which the needle moves and is adapted to hold the catheter, the septum and the distribution channel.

Advantageously, the insertion device 1 is integrated in a frame forming a first housing 20 adapted to be assembled with a second housing 50 comprising means for controlling a piston associated with the reservoir and means for controlling the insertion device 1.

The invention also relates to a method for assembling a needle insertion device. In this method, the first return means 5, the second return means 7 and the needle housing 24 equipped with the needle 21 are assembled. The second return means 7 and the first return means 5 are compressed between parts of the insertion device 1. In the embodiments described, the first return means 5 is compressed between the first rod 41 and the catheter holder 31, and the second return means 7 is compressed between the needle housing 24 and the catheter holder 31. These parts 41, 31, and 24 are adapted to be moved with respect to each other when using the insertion device 1.

The embodiments described include:

assembling the second return means 7, the needle housing 24 and a catheter holder 31 equipped with a catheter 30, the second return means 7 being compressed between the needle housing 24 and the catheter holder 31, attaching the second return means 7, the needle housing 24 and the catheter holder 31, with a first return means 5, on a receiving body 22, the first return means 5 being compressed between the catheter holder 31 and the receiving body 22.

The various components of the insertion device are arranged with respect to each other to obtain an insertion device that is compact, robust and reliable in which the functions for moving the needle housing from its pre-insertion position to its insertion position and for moving the needle housing from its insertion position to its retracted position are clearly separated and performed by different components.

The invention is not limited to the embodiments described and other embodiments will be clearly apparent to those skilled in the art.

The invention claimed is:

1. A device for inserting a needle into a site, comprising:
a support wall on the site,
a receiving body having a guiding housing,
a needle housing, on which an insertion needle is mounted, movably mounted in the guiding housing between
a pre-insertion position in which the needle is retracted with respect to the support wall,
at least one insertion position in which the needle protrudes with respect to the support wall, and
at least one retracted position, in which the needle is again retracted with respect to the support wall,
a first return member, configured to be stressed when the needle housing is in the pre-insertion position and to drive the needle housing from the pre-insertion position to the at least one insertion position in released state,
a second return member, configured to be stressed when the needle housing is in the pre-insertion position and in the at least one insertion position and to drive the needle housing from the at least one insertion position to the at least one retracted position in released state,
a catheter movably mounted with respect to the needle and a catheter holder configured to move the catheter with the needle when the needle housing moves from the pre-insertion position to the at least one insertion position and to separate the catheter from the needle so that the catheter movement remains locked when the needle housing moves from the at least one insertion position to the at least one retracted position, and
a first rod movably mounted in rotation about an axis of rotation (R) in a first rod housing of the receiving body, the axis of rotation (R) being parallel to a guiding axis (G) of the guiding housing receiving the needle housing,
the catheter holder and the first rod comprising a first releasable blocking member which, when released, allows the needle housing to move from the pre-insertion position to the at least one insertion position.

2. The device for inserting the needle according to claim 1, wherein the first return member is mounted around or inside the first rod.

3. The device for inserting the needle according to claim 1, wherein the first rod further comprises a protrusion configured to interact with an activating element to allow the first rod to rotate.

4. The device for inserting the needle according to claim 1, further comprising a retractable locking-member for locking the needle housing with respect to the catheter holder, the retractable locking member comprising:
a stop abutment carried by the catheter holder, and
an elastic tab carried by the needle housing, the elastic tab of the needle housing configured to be clipped under the stop abutment of the catheter holder when the needle housing is in the pre-insertion position, and to be deformed, when the needle housing is in the at least one insertion position, by a ledge carried by the receiving body, such that the needle housing is retracted from the catheter holder.

5. The device for inserting the needle according to claim 1, further comprising a second rod mounted about a longitudinal axis (L) in a second rod housing of the receiving body, the longitudinal axis (L) being parallel to a guiding axis (G) of the guiding housing receiving the needle housing, the second return member being mounted around or inside the second rod.

6. A device for inserting a needle into a site, comprising:
a support wall on the site,
a receiving body having a guiding housing,
a needle housing, on which an insertion needle is mounted, movably mounted in the guiding housing between
a pre-insertion position in which the needle is retracted with respect to the support wall,
at least one insertion position in which the needle protrudes with respect to the support wall, and
at least one retracted position, in which the needle is again retracted with respect to the support wall,
a first return member, configured to be stressed when the needle housing is in the pre-insertion position and to drive the needle housing from the pre-insertion position to the at least one insertion position in released state, and
a second return member, configured to be stressed when the needle housing is in the pre-insertion position and in the at least one insertion position and to drive the needle housing from the at least one insertion position to the at least one retracted position in released state,
wherein the first return member and the second return member extend respectively along a first axis (R) and a second axis (L) that are parallel to a guiding axis (G)

of the guiding housing, the first axis (R) and the second axis (L) being offset transversally with respect to each other.

7. The device for inserting the needle according to claim 6, wherein the needle extends along a needle axis that is parallel to the guiding axis (G), the needle axis being offset transversally with respect to the first axis (R) and the second axis (L).

8. The device for inserting the needle according to claim 6, wherein the first return member is mounted around or inside the first rod.

9. The device for inserting the needle according to claim 6, wherein the first rod further comprises a protrusion configured to interact with an activating element to allow the first rod to rotate.

10. The device for inserting the needle according to claim 6, further comprising:

a catheter movably mounted with respect to the needle and a catheter holder configured to move the catheter with the needle when the needle housing moves from the pre-insertion position to the at least one insertion position and to separate the catheter from the needle so that the catheter movement remains locked when the needle housing moves from the at least one insertion position to the at least one retracted position.

11. The device for inserting the needle according to claim 10, further comprising:

a first rod movably mounted in rotation about an axis of rotation (R) in a first rod housing of the receiving body, the axis of rotation (R) being parallel to a guiding axis (G) of the guiding housing receiving the needle housing, the catheter holder and the first rod comprising a first releasable blocking member which, when released, allows the needle housing to move from the pre-insertion position to the at least one insertion position.

12. The device for inserting the needle according to claim 10, further comprising a second rod mounted about a longitudinal axis (L) in a second rod housing of the receiving body, the longitudinal axis (L) being parallel to a guiding axis (G) of the guiding housing receiving the needle housing, the second return member being mounted around or inside the second rod.

13. The device for inserting the needle according to claim 6, further comprising:

a retractable locking member for locking the needle housing with respect to the catheter holder, the retractable locking member comprising:

a stop abutment carried by the catheter holder, and an elastic tab carried by the needle housing, the elastic tab of the needle housing configured to be clipped under the stop abutment of the catheter holder when the needle housing is in the pre-insertion position, and to be deformed, when the needle housing is in the at least one insertion position, by a ledge carried by the receiving body, such that the needle housing is retracted from the catheter holder.

14. A method for assembling the device for inserting the needle according to claim 1, comprising a step of assembling the first return member, the second return member, and the needle housing equipped with the needle, the second return member and the first return member being compressed between parts of the insertion device that are configured to be moved with respect to each other when using the insertion device.

15. The assembly method according to claim 14, further comprising steps of:

assembling the second return member, the needle housing and a catheter holder equipped with a catheter, the second return member being compressed between the needle housing and the catheter holder, and attaching the second return member, the needle housing and the catheter holder with the first return member on a receiving body, the first return member being compressed between the catheter holder and the receiving body.

16. A system for dispensing a product into a site, comprising:

the device for inserting the needle according to claim 1, and a reservoir containing the product.

17. The system for dispensing the product according to claim 16, further comprising:

a pump connecting the reservoir to the insertion device to dispense the product to the site via the needle.

18. A kit for dispensing a product into a site, comprising a disposable part housing the device for inserting a needle according to claim 1, and a reusable part comprising at least one of a setting device and a control member configured to control the device for inserting the needle.

19. The kit according to claim 18, wherein the disposable part is removably mounted on the reusable part.

20. The kit according to claim 18, further comprising a motor housed in the disposable part.

* * * * *